United States Patent
Liu et al.

(10) Patent No.: US 10,722,123 B2
(45) Date of Patent: Jul. 28, 2020

(54) METHOD FOR DETECTING AT LEAST ONE OF A HEART RATE AND A RESPIRATORY RATE OF A SUBJECT

(71) Applicants: IMEC vzw, Leuven (BE); Stichting IMEC Nederland, Eindhoven (NL)

(72) Inventors: Yao-Hong Liu, Eindhoven (NL); Marco Mercuri, Eindhoven (NL)

(73) Assignees: IMEC vzw, Leuven (BE); Stiching IMEC Nederland, Eindhoven (NL)

( * ) Notice: Subject to any disclaimer, the term of this patent is extended or adjusted under 35 U.S.C. 154(b) by 567 days.

(21) Appl. No.: 15/373,322

(22) Filed: Dec. 8, 2016

(65) Prior Publication Data

US 2017/0172425 A1    Jun. 22, 2017

(30) Foreign Application Priority Data

Dec. 21, 2015 (EP) .................................. 15201670

(51) Int. Cl.
*A61B 5/0205* (2006.01)
*A61B 5/05* (2006.01)
(Continued)

(52) U.S. Cl.
CPC ............ *A61B 5/0205* (2013.01); *A61B 5/024* (2013.01); *A61B 5/05* (2013.01); *A61B 5/0507* (2013.01);
(Continued)

(58) Field of Classification Search
CPC ......... A61B 5/0205; A61B 5/024; A61B 5/05; A61B 5/0507; A61B 5/0803;
(Continued)

(56) References Cited

U.S. PATENT DOCUMENTS 4,122,427 A * 10/1978 Karsh .................... A61B 5/113
367/89
4,513,748 A    4/1985 Nowogrodzki et al.
(Continued)

FOREIGN PATENT DOCUMENTS

| JP | 2011050604 | 3/2011 |
| WO | WO 2007/136610 | 11/2007 |
| WO | WO 2010/030238 | 3/2010 |

OTHER PUBLICATIONS

Extended European Search Report dated Jun. 8, 2016 in European Application No. 15201670.5-1666.
(Continued)

*Primary Examiner* — Christopher L Cook
(74) *Attorney, Agent, or Firm* — Knobbe, Martens, Olson & Bear, LLP

(57) ABSTRACT

A method and system for detecting at least one of a heart rate and a respiratory rate of a subject are disclosed. In one aspect, the method includes transmitting a signal towards the subject and receiving a reflected signal from the subject being Doppler-shifted due to at least one of the heart rate and the respiratory rate. The method also includes providing the reflected signal to a first input of a phase comparator, providing an adjustable reference signal to a second input of the phase comparator, and generating an output signal by the phase comparator based on the reflected signal and the reference signal. The method includes varying, by the reference signal generator, at least one of a phase and a frequency of the adjustable reference signal based on the output signal of the phase comparator to track a phase of the reflected signal.

16 Claims, 2 Drawing Sheets

(51) Int. Cl.
*A61B 5/113* (2006.01)
*A61B 5/08* (2006.01)
*A61B 5/00* (2006.01)
*A61B 5/024* (2006.01)

(52) U.S. Cl.
CPC .......... *A61B 5/0803* (2013.01); *A61B 5/0816* (2013.01); *A61B 5/1135* (2013.01); *A61B 5/7228* (2013.01); *A61B 5/7278* (2013.01)

(58) Field of Classification Search
CPC ... A61B 5/0816; A61B 5/1135; A61B 5/7228; A61B 5/7278
See application file for complete search history.

(56) References Cited

U.S. PATENT DOCUMENTS

| | | | | |
|---|---|---|---|---|
| 4,958,638 | A * | 9/1990 | Sharpe | A61B 5/0205 600/407 |
| 2010/0152600 | A1* | 6/2010 | Droitcour | A61B 5/05 600/534 |
| 2011/0279275 | A1* | 11/2011 | Horng | A61B 5/0205 340/573.1 |
| 2012/0235689 | A1* | 9/2012 | Jau | A61B 5/0205 324/629 |

OTHER PUBLICATIONS

Wu et al., Phase- and Self-Injection—Locked Radar for Detecting Vital Signs with Efficient Elimination of DC Offsets and Null Points, IEEE Transactions on Microwave Theory and Techniques, Jan. 2013, vol. 61, No. 1, pp. 685-695.

* cited by examiner

METHOD FOR DETECTING AT LEAST ONE OF A HEART RATE AND A RESPIRATORY RATE OF A SUBJECT

CROSS-REFERENCE TO RELATED APPLICATIONS

This application claims foreign priority to European Patent Application No. 15201670.5, filed Dec. 21, 2015, the contents of which are incorporated by reference herein in its entirety.

BACKGROUND

Technological Field

The present disclosure relates to a method for detecting at least one of a heart rate and a respiratory rate of a subject.

Description of the Related Technology

In recent years, contactless vital signs monitoring has been an increasingly active field of research. The sensing of vital signs can be made contactless and therefore non-invasive by adopting radar techniques. The Doppler shifts caused by the mechanical movements of the heart and the lungs can be detected and analyzed to determine the heart rate and the respiration rate.

A continuous-wave (CW) radar, also known as a Doppler radar, transmits a radio frequency single-tone continuous-wave signal which is reflected by a target and then demodulated in a receiver. By the Doppler effect, the radio frequency signal reflected by the moving tissue of the target undergoes a frequency shift proportional to the surface velocity of the tissue. If the moving tissue has a periodic motion (as the tissue in the chest region of a subject may have due to the periodic motion of the heart and the lungs) the Doppler effect results in a phase shift of the reflected radio frequency signal which is proportional to the instantaneous surface displacement. In the receiver, the transmitted signal may be mixed with the reflected Doppler-shifted signal to produce a mixing product which, following low pass filtering, results in a baseband signal including a low frequency component that is directly proportional to the instantaneous surface displacement.

However, extraction of the low frequency component from the baseband signal in the Doppler radar-based approach requires that the maximum amplitudes of the chest region displacements due to the heart beat and the respiration are much smaller than the wavelength of the radio frequency signal. This may be referred to as the small angle approximation. Assuming, for a typical subject, an average maximum amplitude of the chest tissue displacements due to the heart beat and the respiration of about 0.08 mm and 0.8 mm, respectively, this condition may be easily satisfied by, for example, using a radio frequency signal with $\lambda=0.125$ in (2.4 GHz) yielding a maximum phase shift of approximately 5 degrees. The baseband signal may still include some non-linear terms (such as inter-modulation products between the heart rate and the respiration rate), but the terms which are linearly proportional to the instantaneous tissue displacement due to the heart rate and the respiration rate will tend to dominate. However, a tissue displacement of merely 8 mm will produce a phase shift of about 46 degrees and violate the small angle approximation. This implies that in case of random movements of the subject causing a random displacement of the reflecting tissue, reliable extraction of the heartbeat and respiration rates from the baseband signal is severely hampered.

A further condition for extraction of the low frequency component from the baseband signal in the Doppler radar-based approach is that the fixed phase offset between the transmitted signal and the reflected signal (i.e. the part of the phase shift not being due to the Doppler-shift, such as the mean distance between the radar and the subject, the reflection at the subject and radio block delay) is an odd multiple of $\pi/2$. This may be referred to as the optimum operation point (or shorter "optimum point") of the Doppler radar. Unless this condition is met, a mathematical analysis of the mixing product reveals that the baseband signal will be distorted by non-linear terms doubling and mixing the frequency components corresponding to the heart rate and the respiration rate. Furthermore frequency components corresponding to the heart rate and the respiration rate will be multiplied by the total residual phase noise between the transmitter and the receiver, thereby degrading the signal-to-noise-ratio. This issue will be particularly pronounced when the fixed phase offset between the transmitted signal and the reflected signal is an integer multiple of $\pi$. This may be referred to as the null operation point (or shorter "null point") of the Doppler radar.

The null points and the optimum points are distributed alternately and are separated by $\lambda/8$, where $\lambda$ represents the wavelength of the transmitted signal. At the commonly used operating radio frequencies, the distance between an adjacent null point and optimum point is in the order of few millimeters or centimeters. For example, at 2.4 GHz this distance is about 1.5 cm. Therefore, obtaining a reliable measurement at the optimum point is in practice very difficult to achieve. Meanwhile, reducing the operating frequency will increase null point-optimum point separation but also will decrease the sensitivity in detecting the vital signs parameters.

Wu et al. proposes in "Phase- and Self-Injection-Locked Radar for Detecting Vital Signs with Efficient Elimination of DC Offsets and Null Points" (IEEE Transactions on Microwave Theory and Techniques, Vol. 61, No. 1, pp. 685-695, January 2013) an alternative Doppler radar system for vital signs monitoring which employs a phase- and self-injection-locked (PSIL) oscillator. A fine tuning voltage for a dual-tuning voltage-controlled oscillator (VCO) is controlled by a phase-locked loop (PLL) to extract the Doppler-shifted signal. The output signal of the VCO is fed to both the transmitting antenna and a phase frequency detector (PFD) of the PLL. The received Doppler-shifted signal is injected into the VCO through a circulator to form an SIL loop. The SIL loop is phase-locked by the PLL to stabilize the output frequency. A Doppler-shifted injection signal will result in an output phase perturbation of the VCO. The phase perturbation is detected by the PFD comparing the Doppler-shifted injection signal to an output signal of a fixed frequency reference oscillator. A charge pump (CP) circuit and a loop filter transforms the output of the PFD into a fine tuning voltage for tuning the intrinsic oscillation frequency of the VCO. Provided the maximum amplitude of the displacement of the target is much smaller than the free-space wavelength of the transmitted signal, the VCO fine tuning voltage controlled by the PLL reflects the phase variation of the Doppler signal due to the heartbeat. Hence, this architecture also relies on the small angle approximation. Furthermore, the PSIL radar exhibits "null points" since there will be points at which there is a zero power spectral SNR gain wherein detection of a displacement is prevented. Therefore, a path diversity switch is employed to periodically switch between two transmission paths presenting a phase difference of $\pi/2$. However, the null point problem may still only be mitigated by the path diversity switch provided the small angle approximation is valid.

SUMMARY OF CERTAIN INVENTIVE ASPECTS

In view of the above, a general objective of the present disclosure is to enable contactless detection of at least one of a heart rate and a respiratory rate of a subject by means which are less sensitive to subject distance and random movements of the subject and which do not rely on the small angle approximation. Further objects may be understood from the following.

According to an aspect of the present disclosure there is provided a method for detecting at least one of a heart rate and a respiratory rate of a subject, the method comprising:

transmitting a radio frequency signal towards the subject;

receiving a reflected signal from the subject, the reflected signal being Doppler-shifted due to at least one of the heart rate and the respiratory rate;

providing the received reflected signal to a first input of a phase comparator;

generating an adjustable reference signal by a reference signal generator and providing the reference signal to a second input of the phase comparator;

generating an output signal by the phase comparator based on the received signal and the reference signal; and varying by the reference signal generator at least one of a phase and a frequency of the adjustable reference signal based on the output signal of the phase comparator to track a phase of the reflected signal.

By feeding back the output signal of the phase comparator to the reference signal generator and adjusting at least one of a phase and a frequency of the reference signal output by the reference signal generator, the phase comparator and the reference signal generator forms a phase-locked loop which tracks frequency and phase variations of the reflected signal. Thereby a demodulated output signal may be provided which represents the time-dependent frequency or phase shift of the reflected signal caused by tissue displacement due to the heart rate and/or the respiratory rate.

The output signal of the phase comparator may thus be indicative of at least one of the heart rate and the respiratory rate. In particular the output signal may include a component which oscillates at a frequency corresponding to the heart rate and a component which oscillates at a frequency corresponding to the respiration rate. Signal components indicative of at least one of the heart rate and the respiratory rate may hence be extracted from the reflected signal.

In accordance with the present disclosure, neither the small angle approximation nor the avoidance of "null points" are conditions for accurate determination of vital signs, as in the prior art approaches. As a result, the heart rate and respiration rate may be determined even in the presence of random movements of tissue of the subject reflecting the transmitted signal. This may be understood by considering that in a steady state of the phase locked loop, the output signal of the phase comparator is independent of the fixed phase offset between the transmitted signal and the reflected signal (i.e. the part of the phase offset not being due to the Doppler-shift, such as the distance to the subject, the reflection at the subject, radio block delay). A random step change of the fixed phase shift results in a step change of the phase of the reflected signal at the first input of the phase comparator. The phase comparator will accordingly generate an output signal which will control the reference signal generator to track the step change of the phase of the reflected signal and, after a transient period, lock on to the phase of the reflected signal at the first input of the phase comparator. Effects in the output signal of the phase comparator due to a (given or changed) fixed phase offset may hence be avoided.

The phase locked loop may hence perform down-conversion of the reflected signal to provide a baseband output signal indicative of a frequency or phase difference between the reflected signal and the adjustable reference signal received at the first and the second input of the phase comparator, respectively. The difference corresponds to the modulation of the reflected signal induced by tissue movement caused by the heartbeat and respiration of the subject.

The phase and/or frequency of the adjustable reference signal may be adjusted to track a phase of the reflected signal with a predetermined offset. As may be understood by the person skilled in the art the predetermined offset may generally depend on the transfer characteristics of the phase comparator. Hence the frequency and/or phase of the reference signal may be varied such that the reference signal tracks the phase in a lagging or synchronous manner.

The radio frequency signal may be transmitted towards a chest region of the subject. The reflected signal may accordingly be Doppler-shifted due to tissue displacement in the chest region caused by at least one of the heart rate and the respiratory rate. The displaced tissue reflecting the transmitted signal may include any one, or a combination, of the chest wall, the heart and the lung(s) of the subject.

According to one embodiment, at least one of the heart rate and the respiratory rate may be determined by performing a frequency analysis of the output signal of the phase comparator. Hence, the desired vital sign(s) may be identified from the output signal by appropriate frequency analysis techniques, such as Fast Fourier Transform. The output signal of the phase comparator may be filtered by a loop filter prior to performing the frequency analysis.

According to one embodiment the method further comprises integrating the output signal from the phase comparator. By integrating the output signal the signal level of the output signal may be increased, thereby simplifying further analysis. Also, by integrating the output signal the time-varying phase variations of the reflected signal resulting from the heart rate and the respiratory rate may be obtained. The heart rate and/or the respiration rate may thereby be readily identified and interpreted from the integrated signal since the output signal represents a superposition of the mechanical movements due to the heartbeat and the breath and other movement of the tissue reflecting the transmitted signal. Accordingly, the heart rate and/or respiration rate may be determined by performing a frequency analysis of the integrated output. The output signal of the phase comparator may be filtered by a loop filter prior to being integrated.

On the basis of the integrated output of the phase comparator, a magnitude of a tissue displacement due to at least one of the heart rate and the respiratory rate may be estimated by determining an amplitude of a frequency component of the integrated output. Hence, information regarding the magnitude of the mechanical movement of the heart and/or the lungs may be extracted from the reflected signal.

According to one embodiment the phase comparator includes a mixer. A mixer provides a simple and cost-effective implementation of a phase comparator. The mixer may generate an output signal oscillating at the difference frequency between the reflected signal received at the first input and the adjustable reference signal received at the second input. The method may further comprise filtering the output signal of the mixer to suppress frequency components above the difference frequency, such as a frequency component at the sum frequency of the reflected signal and the adjustable reference signal, and optionally higher order inter-modulation products.

According to one embodiment the reference signal generator includes a voltage controlled oscillator. A voltage controlled oscillator provides a simple and cost-effective implementation of an adjustable reference signal generator.

According to one embodiment the reference signal generator includes an oscillator and a phase modulator. The phase modulator may vary the phase of the reference signal generated by the oscillator to track the phase of the reflected signal.

The method may further comprise integrating the output signal of the phase comparator and providing the integrated output signal to the phase modulator. The phase of the adjustable reference signal may hence be varied based on the integrated output signal to track a phase of the reflected signal.

According to one embodiment the adjustable reference signal is generated with a phase which is correlated to a phase of the transmitted signal. Thereby phase noise in the output of the phase comparator may be minimized due to correlation between the transmitted signal and the reference signal. This improves the accuracy of the method. In particular the transmitted radio frequency signal and the reference signal may be generated by a common oscillator.

According to one embodiment the radio frequency signal transmitted towards the subject is a fixed-frequency signal. This may simplify the hardware implementations of the transmitter- and the receiver-side. In particular the radio frequency signal transmitted towards the subject may be a continuous wave radio frequency signal of a fixed frequency.

According to another aspect of the present disclosure there is provided a system for detecting at least one of a heart rate and a respiratory rate of a subject, the system comprising:

a transmitter adapted to transmit a radio frequency signal towards the subject;

a receiver adapted to receive a reflected signal from the subject, the reflected signal being Doppler-shifted due to at least one of the heart rate and the respiratory rate;

a phase comparator adapted to receive the reflected signal at a first input of the phase comparator and to receive an adjustable reference signal at a second input of the phase comparator and to provide an output signal based on the received signal and the adjustable reference signal; and a reference signal generator adapted to output the adjustable reference signal, wherein the reference signal generator is adapted to vary at least one of a phase and a frequency of the adjustable reference signal based on the output signal of the phase comparator to track a phase of the reflected signal.

The details and advantages discussed in connection with the method aspect above applies correspondingly to the present system wherefore reference is made to the above discussion.

The phase comparator and the reference signal generator form part of a phase-locked loop of the system which tracks the phase of the reflected signal.

The system may include a loop filter adapted to filter the output signal received from the phase comparator. The filtered output signal may be provided as a feedback signal to the reference signal generator wherein the reference signal generator may be adapted to vary at least one of a phase and a frequency of the adjustable reference signal based on the filtered output signal.

The system may include a processing unit adapted to determine at least one of the heart rate and the respiratory rate by performing a frequency analysis of the output signal of the phase comparator (which may be filtered by the loop filter prior to being received at the processing unit).

The system may include an integrator adapted to integrate the output signal from the phase comparator (which may be filtered by the loop filter prior to being received at the integrator).

The phase comparator may include a mixer.

The reference signal generator may include a voltage controlled oscillator.

The reference signal generator may include an oscillator and a phase modulator.

The reference signal generator may include an oscillator and a phase modulator and the system may further comprise an integrator adapted to integrate the output signal from the phase comparator (which may be filtered by the loop filter prior to being received at the integrator) and provide the integrated output signal to the phase modulator. The phase modulator may be adapted to vary a phase of the adjustable reference signal based on the integrated output signal to track a phase of the reflected signal.

The reference signal generator may be adapted to generate the adjustable reference signal with a phase which is correlated to a phase of the transmitted signal.

The radio frequency signal transmitted towards the subject may be a fixed-frequency signal.

BRIEF DESCRIPTION OF THE DRAWINGS

The above, as well as additional objects, features and advantages of the present disclosure, will be better understood through the following illustrative and non-limiting detailed description of embodiments of the present disclosure, with reference to the appended drawings. In the drawings like reference numerals will be used for like elements unless stated otherwise.

DETAILED DESCRIPTION OF CERTAIN ILLUSTRATIVE EMBODIMENTS

Figure 1:
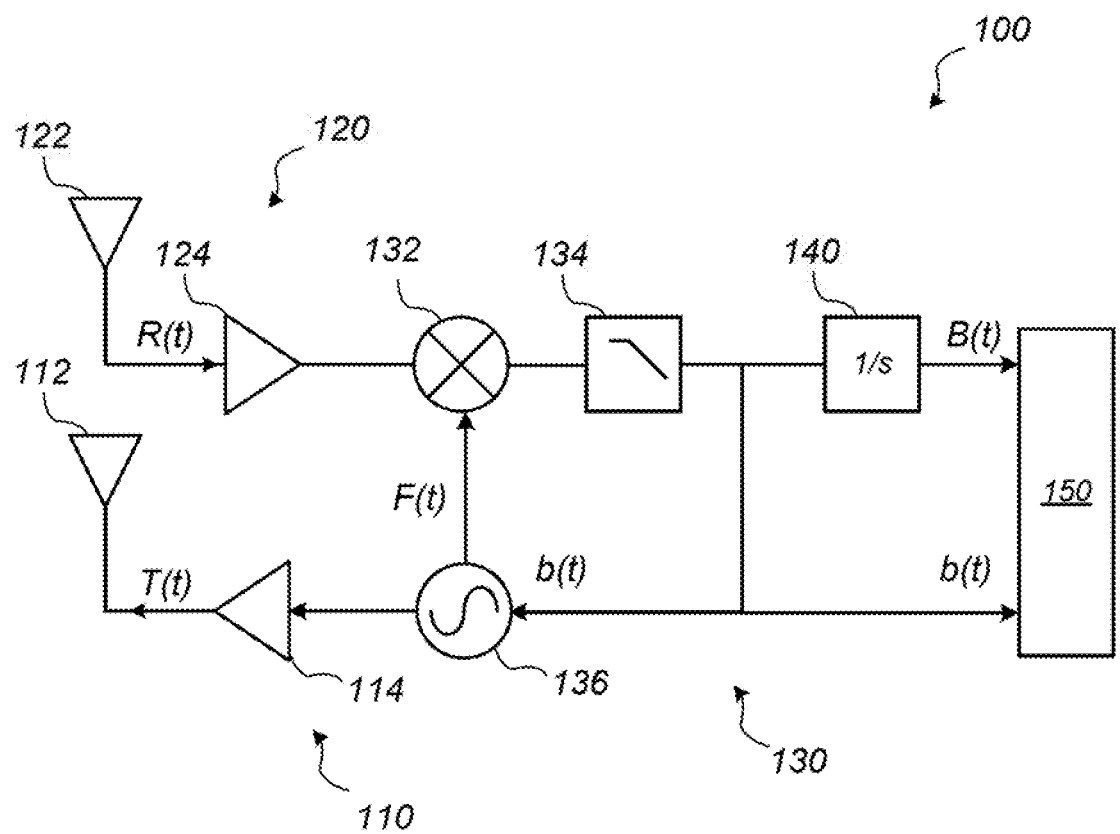
FIG. 1 is a schematic block diagram of a first system which may be used for determining a heart rate and/or a respiratory rate of a subject according to the present disclosure.

FIG. 1 is a schematic block diagram of a first system 100 which may be used for detecting and determining a heart rate and/or a respiratory rate of a subject. The subject may be a human, however the present disclosure is equally applicable to other mammal or animal subjects. In the following description the subject may also be referred to as the "target."

The system 100 includes a transmitter 110 arranged to transmit a radio frequency signal T(t) towards the subject. The signal T(t) is generated by a signal generator 136 which will be described in detail below. The signal T(t) is transmitted towards the subject via a transmitter antenna 112. The transmitter 110 may optionally include an amplifier 114 for amplifying the signal generated by the signal generator 136 prior to transmission by the transmitter antenna 112. The transmitter 110 may for example be arranged to generate the signal T(t) with a frequency in the range of 300 MHz to 300 GHz.

The system 100 further includes a receiver 120 arranged to receive a radio frequency signal R(t) resulting from a reflection of the transmitted signal T(t) by the subject. The reflected signal R(t) may be received via a receiver antenna 122. The receiver 120 may optionally include an amplifier 124 for amplifying the received signal R(t) prior to demodulation thereof.

Each one of the transmitter antenna 112 and the receiver antenna 122 may for instance be arranged as a patch antenna, a beamforming antenna or a horn antenna.

For the purpose of detecting the heart rate and/or respiratory rate the transmitter 110 is advantageously oriented such that the transmitted signal T(t) is directed towards a chest region of the subject. Correspondingly, the receiver 120 is advantageously oriented such as to receive the reflected signal R(t) from the chest region of the subject.

The heartbeat and the respiration of the subject cause a respective periodic motion or displacement of the tissue in the chest region of the subject. Assuming that the subject is facing in the direction of the transmitter 110 and the receiver 120, the tissue in the chest region of the subject will, due to the heartbeat and respiration, exhibit a tune-varying displacement along the direction of propagation of the transmitted signal T(t) and the reflected signal R(t). Upon reflection of the transmitted signal T(t) the displacement will result in a time-varying Doppler-shift of the reflected signal R(t). In other words the heartbeat and the respiration of the subject will result in a modulation (which may be expressed as a time-varying frequency or phase shift) of the reflected signal R(t).

In order to demodulate or extract the phase/and or frequency modulation of the reflected signal R(t), caused by the displacement of the tissue, the system 100 employs a phase-locked loop (PLL) 130. As may be understood from the following, the PLL 130 operates in a frequency-demodulator configuration.

The PLL 130 includes a phase comparator 132. The phase comparator 132 includes a first input and a second input. As illustrated in FIG. 1, the phase comparator 132 may be implemented as a mixer. The mixer may be for instance a diode mixer, a diode ring mixer, a switching mixer, a Gilbert cell mixer or some other type of frequency-conversion mixer. The mixer may be a balanced or double-balanced mixer. However, other types of phase comparators 132 may also be used such as a phase-frequency detector (a charge-pump phase detector or an exclusive-OR type of phase comparator). The phase comparator 132 is arranged to detect a phase difference between the reflected signal R(t) received at the first input and an adjustable reference signal F(t) received at the second input from the signal generator 136. The phase comparator 132 is arranged to provide an output signal which is indicative of a phase difference between the reflected signal R(t) and the adjustable reference signal F(t).

For an idealized phase comparator, the output signal or error signal $V_e(t)$ may be characterized as:

$$V_e(t) = K_{PC} \Delta\varphi(t) \quad \text{(Equation 1)}$$

where $K_{PC}$ represents the gain of the phase comparator and $\Delta\varphi(t)$ represents the instantaneous phase difference between the reflected signal R(t) and the reference signal F(t). For a mixer-type phase comparator, the output signal $V_e(t)$ will include the mixing product of the reflected signal R(t) and the reference signal F(t) and may thus include both a component oscillating at a frequency corresponding to a sum of the frequency of R(t) and the frequency of F(t) and a term oscillating at a frequency corresponding to the difference between the frequency of R(t) and the frequency of F(t). The higher frequency term may be low pass filtered (e.g., using the loop filter 134 described below) wherein the resulting error signal takes the form:

$$V_e(t) = K_m R_0 F_0 \cos[(\omega_R - \omega_F)t + \Delta\varphi(t)] \quad \text{(Equation 2)}$$

where $K_m$ represents the gain of the mixer; $R_0$ and $F_0$ represent the amplitudes of R(t) and F(t), respectively; $\omega_R$ and $\omega_F$ represent the angular frequency of R(t) and F(t), respectively; and $\Delta\varphi(t)$ represents the part of the phase shift which is not due to the frequency difference between R(t) and F(t). If $\omega_R = \omega_F$ (implying that the PLL 130 is in a "locked" state), the output signal $V_e(t)$ according to Equation 2 becomes proportional to $\cos[\Delta\varphi(t)]$.

The phase difference which results in a zero signal level output of the phase comparator 132 (hereinafter referred to as the "predetermined phase difference") generally depends on the transfer characteristics of the particular implementation of the phase comparator 132. For example, a phase comparator employing a mixer-based implementation may output a zero signal level when the phase difference is $\pi/2$. Other implementations of a phase comparator may output a zero signal level when the phase difference is 0 degrees, such as a charge pump phase detector.

Accordingly, the level of the output signal $V_e(t)$ of the phase comparator 132 varies as a function of an instantaneous phase difference between the reflected signal R(t) received at the first input of the phase comparator 132 and the adjustable reference signal F(t) received at the second input of the phase comparator 132.

The PLL 130 includes a loop filter 134 arranged to filter the output signal $V_e(t)$ of the phase comparator 132. The filtered output signal b(t) is provided as a feedback signal to the signal generator 136. The loop filter 134 may be implemented as a low-pass filter with a cut-off frequency higher than an expected maximum frequency of the heart rate and/or the respiration rate. For the purpose of suppressing components oscillating at and above a frequency corresponding to a sum of the frequencies of the reflected signal R(t) and the reference signal F(t), the cut-off frequency is preferably lower than the sum. Accordingly, components of the output signal $V_e(t)$ having frequencies above the difference frequency may be suppressed in the feedback signal b(t).

For the purpose of detection of heart rate or respiration rate an upper limit of the frequency range of main interest may be 10-20 Hz. Accordingly the loop filter 134 may be adapted to suppress frequencies above 10-20 Hz (i.e., by providing a cut off frequency falling in the range 10-20 Hz). However, for the purpose of obtaining a loop characteristic of the PLL 130 such that the PLL 130 may reliably track the frequency/phase shift of R(t) due to tissue displacement caused by the heartbeats and/or respiration, the loop filter 134 may be adapted to suppress frequencies above a threshold frequency in the range of one or a few kHz to one or two MHz (i.e., by providing a cut off frequency falling in the range 1 kHz to 2 MHz).

As shown in FIG. 1, the signal generator 136 includes a transmission signal output and a reference signal output. The signal generator 136 is arranged to output the radio frequency signal T(t) to be transmitted towards the subject via the transmission signal output. The signal generator 136 is arranged to output the adjustable reference signal F(t) via the reference signal output.

The signal generator 136 is arranged to generate the transmission signal T(t) at a fixed frequency. In particular, the transmission signal T(t) may form a fixed frequency continuous wave signal. On the other hand, the signal generator 136 is arranged to generate the reference signal F(t) with a variable frequency which is controlled on the basis of the feedback signal b(t). In particular, the signal generator 136 is arranged to vary the frequency of the feedback signal F(t) to track a phase of the reflected signal R(t). The reference signal F(t) may form a variable frequency continuous wave signal.

The signal generator 136 may include a voltage controlled oscillator (VCO) having a control input for receiving the feedback signal b(t). The VCO provides the reference signal F(t) at the reference signal output with a frequency which varies with the signal level of the feedback signal b(t) received at the control input.

In response to a phase difference between the reflected signal R(t) and the adjustable reference signal F(t) increasing above the predetermined phase difference (i.e., determined by the transfer characteristics of the phase comparator 132), the signal level of the feedback signal b(t) increases above zero wherein the frequency of the adjustable reference signal F(t) is increased. In response to a phase difference between the reflected signal R(t) and the adjustable reference signal F(t) decreasing below the predetermined phase difference the signal level of the feedback signal b(t) decreases below zero wherein the frequency of the adjustable reference signal F(t) output by the VCO is decreased.

Assuming an idealized VCO, the (angular) frequency $\omega_{out}$ of the reference signal F(t) provided by the VCO varies according to:

$$\omega_{out} = \omega_0 + K_{VCO} V_C(t) \quad \text{(Equation 3)}$$

where $\omega_0$ represents the nominal (i.e., free-running) frequency of the VCO, $K_{VCO}$ represents the gain of the VCO, and $V_C(t)$ represents the signal level at the control input of the VCO. In the system 100, $V_C(t)$ corresponds to b(t).

It may be noted that although the above Equations 1-3 represent idealized output signal models for the respective elements, the equations are approximately valid in a linear operating regime of the elements. At least, the equations are representative for understanding the dynamics of the system 100.

The signal generator 136 may advantageously be arranged to generate and output the reference signal F(t) with a phase which is correlated to a phase of the transmitted signal T(t). The system 100 may thereby provide coherent detection.

This may for example be achieved by the signal generator 136 including an oscillator which is common for the transmitter 110 and the receiver 120. The oscillator may for example be a crystal oscillator. An up-converted transmission signal T(t) may be synthesized by a transmitter-side fractional synthesizer formed by a (first) PLL which is driven by the oscillator output. The feedback signal F(t) may be synthesized by a transmitter-side fractional synthesizer formed by a (second) PLL. The synthesized feedback signal F(t) may be provided to the second input of the phase comparator 132. A VCO of the second PLL may receive as control input a sum of the feedback signal b(t) (i.e., the filtered error signal $V_e(t)$ of the phase comparator 132) and an error signal representing a phase difference between the local oscillator and the (divided-by-N) output of the VCO. This however merely represents one manner of obtaining a coherent system 100 and a coherency may be achieved using other types of dual-output VCOs which are known in the art.

In use of the system 100 for detecting heart rate and/or respiratory rate of a subject, a radio frequency signal T(t) is transmitted by the transmitter 110 towards the chest region of the subject. The transmitted signal T(t) is reflected by tissue of the chest region of the subject. The reflected signal R(t) is received by the receiver 120. As described above, the reflected signal R(t) will be modulated by the time-varying displacement of the tissue emitting the reflected signal R(t).

The total tissue displacement x(t) due to heartbeat and respiration of the subject may be expressed as:

$$x(t) = x_r(t) + x_h(t) = X_r \sin(2\pi f_r t) + X_h \sin(2\pi f_h t) \quad \text{(Equation 4)}$$

where $x_r(t)$ and $x_h(t)$ indicate respectively the mechanical displacements produced by the respiration and the heart. As shown in Equation 4, $x_r(t)$ and $x_h(t)$ may be approximated as periodic functions, where $X_r$ and $X_h$ are the maximum mechanical displacements caused by the expansion and contraction of the lungs and the heart and $f_r$ and $f_h$ are the vital signs frequencies which represent the information to be determined. $X_r$ and $X_h$ may for instance on average be about 0.5-10 mm and 0.05-0.1 mm, respectively, for an adult. Depending on the subject and on the health condition, $f_r$ and $f_h$ generally are within 0.2-3 Hz. These ranges however only represent non-limiting examples and the system 100 is usable for detection of heart rate and/or respiratory rate in even broader ranges of tissue displacement amplitudes and frequencies. It should also be noted that the above approximation only is provided as an example to facilitate understanding of the principles of the present disclosure and the present disclosure is not dependent on a particular choice of approximation.

The reflected signal R(t) is (subsequent to the optional amplification) provided to the first input of the phase comparator 132 where R(t) is compared to the feedback signal F(t) provided to the second input of the phase comparator 132. As described above, the feedback signal F(t) tracks the phase of the reflected signal R(t). Therefore, the feedback signal b(t) (i.e., the filtered output signal $V_e(t)$ of the phase comparator 132) becomes proportional to the modulations induced by the time-varying displacement of the tissue. Assuming a linear output characteristic of the phase comparator 132 the feedback signal is given by Equation 5:

$$b(t) = K_b \left[ \frac{4\pi x_r(t)}{\lambda} + \frac{4\pi x_h(t)}{\lambda} \right] \quad \text{(Equation 5)}$$

where $K_b$ is a combined gain factor for the PLL 130 and $\lambda$ is the wavelength of the transmitted signal T(t). In practice, b(t) further includes a contribution from the residual phase noise of the system 100. The residual phase noise will in general be relatively small in a coherent system and will therefore be neglected in order to improve readability of the description.

The characterization of the feedback signal b(t) in Equation 5 is valid on a condition that the position of the subject is fixed in relation to the system 100. However a main advantage of the system 100 is that it may be used for detecting the heart rate and/or respiration rate even in a non-idealized scenario wherein the distance between the subject/target and the system 100 is not fixed. This may be understood by considering the effect of a step change of the distance between the subject and the system 100. A step change of the distance will result in a step change of the phase difference between the reflected signal R(t) and the reference signal F(t). The PLL 130 will respond to the step change of the phase difference by changing the frequency of the reference signal F(t) to track the phase difference. After a transient (the duration of which is determined by the dynamics of the PLL 130) the PLL 130 will reacquire a lock wherein the reference signal F(t) will catch up/fall back with the phase of the reflected signal R(t). Hence the static target distance $d_o$ has no influence on b(t) in a steady state. As may be understood, this discussion is equally applicable to other sources for static and semi-static phase offsets, such as radio block delay. The PLL 130 will hence force the receiver 120 to operate at its optimum point, which corresponds to the point where a phase difference between the reflected signal R(t) and the feedback signal b(t) is relatively small, wherein the signal level of the low-frequency components of the output signal $V_e(t)$ will be close to zero.

In the event that the chest region of the subject undergoes a periodic movement along the direction of propagation of the transmitted signal T(t) and the reflected signal R(t), it follows from the above that the feedback signal b(t) may be expressed as:

$$b(t) = K_b \left[ \frac{4\pi x_r(t)}{\lambda} + \frac{4\pi x_h(t)}{\lambda} + \frac{4\pi d(t)}{\lambda} \right] \quad \text{(Equation 6)}$$

where the additional term d(t) represents the periodic variation of the target distance about the mean distance $d_0$. The periodic variation may be expressed as:

$$d(t) = X_s \sin(2\pi f_s t) \quad \text{(Equation 7)}$$

where $X_s$ represents the maximum amplitude of the periodic variation of the subject distance and $f_s$ represents the frequency of the variation. Since the feedback signal b(t) is free from any cross terms between the heart rate, the respiration rate and the periodically varying target distance the respective frequencies of the vital signs may be readily distinguished and extracted even in the presence of periodic subject movements. Provided a frequency of the periodic subject movements falls outside the typical range of frequencies of the heart rate and the respiration rate, the signal contribution due to periodic subject movements may even be removed from b(t) by filtering based on a priori knowledge of standard ranges of the heart rate and the respiration rate.

The feedback signal b(t) (according to Equation 5 or Equation 6) represents the frequency variations (i.e., the frequency modulation) of the reflected signal R(t) resulting from the tissue displacement due to the heart beat and respiration (and other periodic chest region movement, if any). The corresponding phase variations B(t) (i.e., the phase modulation) of the reflected signal R(t) may be obtained by passing the feedback signal b(t) through the integrator 140. The integrator may for example be provided in the form of an integrating amplifier or a digital integrator. The integrated output B(t) may be characterized as:

$$B(t) = K_B \left[ \theta + \frac{4\pi X_R(t)}{\lambda} + \frac{4\pi X_H(t)}{\lambda} + \frac{4\pi D(t)}{\lambda} \right] \quad \text{(Equation 8)}$$

where $K_B$ represents the combined gain factor for the PLL 130 and the integrator 140, and $\theta$ is dependent on the integration time of the integrator 140 and the fixed phase shift (which takes into account the reflection at the chest region, the delays between radio blocks, and the target mean distance $d_0$). $X_R(t)$, $X_H(t)$ and D(t) represent the respective primitive functions of $x_r(t)$, $x_h(t)$ and d(t). Assuming that $x_r(t)$, $x_h(t)$ and d(t) may be approximated as harmonic oscillations the primitive functions will only differ from $x_r(t)$, $x_h(t)$ and d(t) by a phase shift of $\pi/2$.

For the purpose of detecting the heart rate and/or the respiratory rate, the system 100 includes a processing unit 150. The processing unit 150 may, as illustrated, receive both the feedback signal b(t) and the integrated feedback signal B(t) as inputs. However, it is also possible for the processing unit 150 to operate on the basis of only b(t) or B(t).

The processing unit 150 may also be arranged to determine or estimate the heart rate and/or the respiratory rate by performing a frequency analysis of the signal b(t) or B(t). The frequency analysis may include determining a frequency of at least one frequency component of the signal b(t) or B(t) within a given frequency interval. The frequency component(s) may be respective frequency components of the signal b(t) or B(t) which fall within the given frequency interval and which have a respective amplitude which exceeds a threshold level. The frequency interval may correspond to an expected frequency range of the vital sign(s) to be determined, i.e., the heart rate and/or the respiratory rate. The frequency interval may, for example, be 0.2-3 Hz. The threshold level may be set such that the influence of noise is minimized without reducing the sensitivity of the measurement too much. The processing unit 150 may output the determined frequency/frequencies as an estimate of the heart rate and/or respiratory rate. The processing unit 150 may identify the component of the two components having the lowest frequency as the respiration rate and the other component as the heart rate. The output may for example be presented on a display connected to the system 100 or stored in a storage device for further analysis and post-processing. The processing unit 150 may further be arranged to estimate a magnitude of a tissue displacement due to at least one of the heart rate and the respiratory rate by determining an amplitude of a frequency component of the integrated output.

In a more basic implementation the processing unit 150 may simply be adapted to detect whether a heart rate and/or a respiratory rate is present, e.g., by determining if the frequency interval includes any component(s) of an amplitude exceeding a (respective) threshold level. The processing unit 150 may accordingly output a signal indicating whether such components were detected or not.

Figure 2:
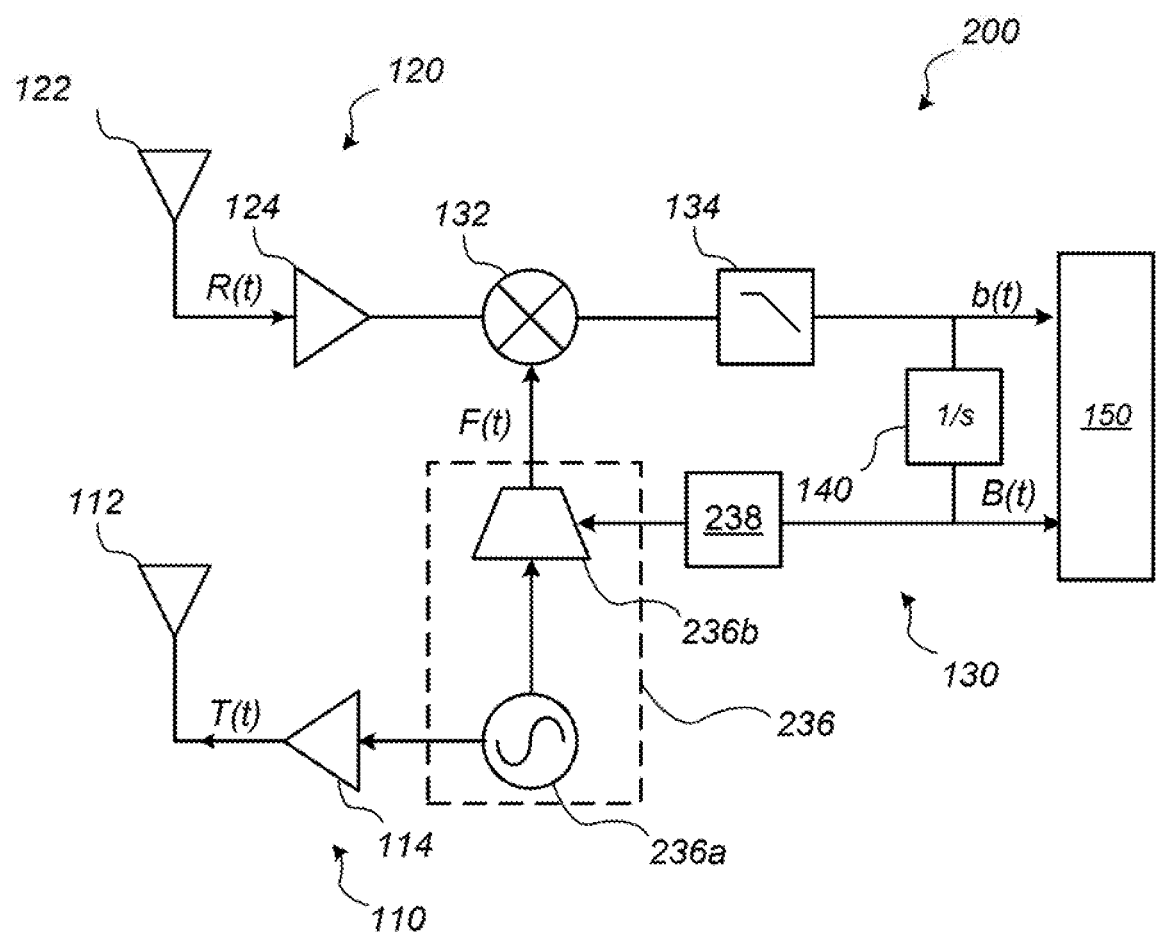
FIG. 2 is a schematic block diagram of a second system which may be used for determining a heart rate and/or a respiratory rate of a subject according to the present disclosure.

FIG. 2 is a schematic block diagram of a second system 200 representing a modification of the first system 100. The elements of the system 200 generally correspond to those of the system 100. Accordingly, the description of an element of the system 100 in FIG. 1 is applicable also to the correspondingly numbered element of the system 200, unless explicitly stated otherwise.

In contrast to the system 100, due to the implementation of the signal generator 236 (which will be described below), the integrator 140 is arranged in the PLL 130. The integrator 140 is arranged to integrate the output of the loop filter 134, i.e., the feedback signal b(t), to provide an integrated feedback signal B(t). As may be understood from the following, the PLL 130 may hence operate in a phase-demodulator configuration.

The system 200 includes a signal generator 236. The function of the signal generator 236 generally corresponds to the function of the signal generator 136 of the system 100. Accordingly, the signal generator 236 includes a transmission signal output and a reference signal output. The signal generator 236 is arranged to output the radio frequency signal T(t) to be transmitted towards the subject via the transmission signal output. The signal generator 236 is arranged to output the adjustable reference signal F(t) at the reference signal output.

The signal generator 236 includes an oscillator 236a. The oscillator 236a is arranged to generate the transmission signal T(t) at a fixed frequency. In particular, the transmission signal T(t) may form a fixed frequency continuous wave signal. The oscillator 236a may for example include a VCO, a crystal oscillator or some other type of electronic oscillator capable of providing a single frequency continuous wave output. The oscillator 236a may include a fractional synthesizer formed by a PLL (not shown) for up-converting the frequency of the electronic oscillator for obtaining a transmission signal T(t) of a desired frequency.

The signal T(t) generated by the oscillator 236a is provided also to a phase selector 236b of the signal generator 236. The phase selector 236b is arranged to generate, on the basis of the signal T(t) and a feedback signal B(t) of the PLL 130, a reference signal F(t) with a particular phase selected from a set of N predetermined phases. The phase selector 236b may for example include a set of N delay blocks arranged to delay a received signal (i.e., the signal T(t) from the local oscillator 236a) by one of:

{0°, 360°/N, 2*360°/N, . . . (N−1)*360°/N}

The phase selector 236b may as another example include a set of N delay blocks arranged to delay a received signal (i.e., the signal T(t) from the local oscillator 236a) by one of:

{0°, 180°/N, 2*180°/N, . . . (N−1)*180°/N}

The phase selector 236b may include a selector circuit (not shown) which, based on the feedback signal B(t) of the PLL 130 selects a particular one of the N delay blocks in order to track a phase of the reflected signal R(t).

The selector circuit may be arranged to select a delay block of a particular delay based on the feedback signal B(t). The feedback signal B(t) may hence be interpreted as a phase command word controlling the selector circuit to select a particular delay block, depending on the signal level of B(t). The signal generator 236 may thereby vary the phase of the feedback signal F(t) to track a phase of the reflected signal R(t). Instead of such a digital implementation of the selector circuit it is also possible to use an analog implementation employing a phase shifter for varying a phase of the feedback signal F(t) in a continuous manner.

The PLL 130 may optionally include a phase wrapping circuit 238 adapted to wrap a phase of the output signal from the integrator 140. The phase wrapping circuit 238 may switch a polarity of the output signal from the integrator 140 if the integrator 140 is saturated. In the event that the integrator 140 is implemented as a digital integrator, the digital integrator may be adapted to perform the wrapping function.

The system 200 may be used for detecting or determining at least one of a heart rate and/or a respiratory rate in a manner which is completely analogous to what was described above in connection with the system 100 wherefore reference is made to the above description.

In the above the present disclosure has mainly been described with reference to a limited number of examples. However, as is readily appreciated by a person skilled in the art, other examples than the ones disclosed above are equally possible within the scope of the present disclosure, as defined by the appended claims.

For example, although the systems 100, 200 have been illustrated in schematic block diagrams, the various electronic elements of the systems 100, 200 may be implemented in one or more integrated circuits. The functions of the processing unit 150 may be implemented in the one or more integrated circuits or by one or more Application-Specific Integrated Circuits (ASICs) or Field-Programmable Gate Arrays (FPGAs), or by a general-purpose processor (such as a CPU) programmed for determining the heart rate and/or the respiration rate.

Furthermore, the systems 100, 200 employ a separate transmitter antenna 112 and a separate receiver antenna 122. However, it is equally possible to instead arrange the transmitter 110 and the receiver 120 to transmit/receive via a common antenna. The transmitter 110 and the receiver 120 may be connected to a common antenna via a circulator or coupler arranged to direct transmitted signals T(t) from the transmitter 110 (e.g., from the transmission output of the signal generator 136 or from the output of the amplifier 114 if present) to the common antenna and to direct reflected signals R(t) from the common antenna to the receiver 120 (e.g., to the first input of the phase comparator 132 or to an input of the amplifier 124 if present). Hence the same antenna may be used for both transmission of the signal T(t) and for reception of the reflected signal R(t).

What is claimed is:

1. A method for detecting at least one of a heart rate and a respiratory rate of a subject, comprising:
   transmitting, via a transmitter antenna, a radio frequency signal towards the subject;
   receiving, via a receiver antenna, a reflected signal from the subject, the reflected signal being Doppler-shifted relative to the radio frequency signal due to at least one of the heart rate and the respiratory rate;
   providing the reflected signal to a first input of a phase comparator;
   generating an adjustable reference signal by a signal generator and providing the adjustable reference signal to a second input of the phase comparator;
   generating an output signal by the phase comparator based on the reflected signal and the adjustable reference signal;
   generating a filtered output signal by filtering the output signal with a filter and providing the filtered output signal to an integrator and a processing system;
   integrating the filtered output signal by the integrator to generate an integrated filtered output signal;
   varying, by the signal generator, at least one of a phase and a frequency of the adjustable reference signal based on the integrated filtered output signal or the filtered output signal to track a phase of the reflected signal; and
   determining, by the processor, the at least one of the heart rate and the respiratory rate of the subject based on at least one of the integrated filtered output signal and the filtered output signal.

2. The method according to claim 1, wherein determining the at least one of the heart rate and the respiratory rate comprises performing a frequency analysis of the filtered output signal.

3. The method according to claim 1, wherein determining the at least one of the heart rate and the respiratory rate comprises performing a frequency analysis of the integrated filtered output signal.

4. The method according to claim 1, further comprising estimating a magnitude of motion of tissue of the subject.

5. The method according to claim 1, wherein the phase comparator includes a mixer.

6. The method according to claim 1, wherein the signal generator includes a voltage controlled oscillator.

7. The method according to claim 1, wherein the reference signal generator includes an oscillator and a phase modulator.

8. The method according to claim 7, wherein providing the integrated filtered output signal to the signal generator comprises providing the integrated filtered output signal to the phase modulator.

9. The method according to claim 1, wherein the adjustable reference signal is generated with a phase which is correlated to a phase of the radio frequency signal.

10. The method according to claim 1, wherein the radio frequency signal transmitted towards the subject is a fixed-frequency signal.

11. A system for detecting at least one of a heart rate and a respiratory rate of a subject, the system comprising:
- a transmitter configured to transmit a radio frequency signal towards the subject;
- a receiver configured to receive a reflected signal from the subject, the reflected signal being Doppler-shifted relative to the radio frequency signal due to at least one of the heart rate and the respiratory rate;
- a phase comparator configured to receive the reflected signal at a first input of the phase comparator and to receive an adjustable reference signal at a second input of the phase comparator, the phase comparator adapted to provide an output signal based on the reflected signal and the adjustable reference signal;
- a filter configured to generate a filtered output signal based on filtering the output signal;
- an integrator configured to integrate the filtered output signal from the filter and provide the integrated output signal to a signal generator;
- the signal generator configured to generate and output the radio frequency signal and the adjustable reference signal, wherein the signal generator is adapted to vary at least one of a phase and a frequency of the adjustable reference signal based on the integrated filtered output signal of the integrator to track a phase of the reflected signal; and
- a processing unit configured to determine the at least one of the heart rate and the respiratory rate based on at least one of the integrated filtered output signal and the filtered output signal.

12. The system of claim 11, wherein the phase comparator and the signal generator form part of a phase-locked loop of the system which tracks the phase of the reflected signal.

13. The system of claim 11, wherein the filter comprises a loop filter.

14. The system of claim 11, wherein the processing unit is configured to determine the at least one of the heart rate and the respiratory rate by performing a frequency analysis of the integrated filtered output signal.

15. The system of claim 11, wherein the adjustable reference signal is generated with a phase which is correlated to a phase of the radio frequency signal.

16. The system of claim 11, wherein the processing unit is configured to determine the at least one of the heart rate and the respiratory rate by performing a frequency analysis of the filtered output signal.

* * * * *